United States Patent [19]

Timm et al.

[11] Patent Number: 4,522,198
[45] Date of Patent: Jun. 11, 1985

[54] PENILE PROSTHESIS

[75] Inventors: Gerald W. Timm, Minneapolis; Donald L. Sandford, Lauderdale; Timothy J. Claude, Coon Rapids; Richard A. Helms, Elk River, all of Minn.

[73] Assignee: Dacomed Corporation, Minneapolis, Minn.

[21] Appl. No.: 485,648

[22] Filed: Apr. 18, 1983

[51] Int. Cl.³ .............................................. A61F 5/00
[52] U.S. Cl. ............................................... 128/79; 3/1
[58] Field of Search ..................... 128/79; 3/1; 52/108

[56] References Cited

U.S. PATENT DOCUMENTS

| | | |
|---|---|---|
| 2,166,589 | 7/1939 | Harrington . |
| 2,822,896 | 2/1958 | Schuster . |
| 2,909,351 | 10/1959 | Pratt . |
| 3,273,813 | 9/1966 | George . |
| 3,349,526 | 10/1967 | Schuster . |
| 3,427,769 | 2/1969 | Star . |
| 3,492,768 | 2/1970 | Schuster . |
| 3,529,797 | 9/1970 | Street . |
| 3,730,186 | 5/1973 | Edmunds, Jr. . |
| 3,750,194 | 8/1973 | Summers . |
| 3,832,996 | 9/1974 | Kalnberz . |
| 3,851,430 | 12/1974 | Schuster . |
| 3,853,122 | 12/1974 | Strauch et al. . |
| 3,893,456 | 7/1975 | Small et al. . |
| 3,954,102 | 5/1976 | Buuck . |
| 3,963,037 | 6/1976 | Clark . |
| 3,987,789 | 10/1976 | Timm et al. . |
| 3,991,752 | 11/1976 | Gerow . |
| 4,009,711 | 3/1977 | Uson . |
| 4,056,095 | 11/1977 | Rey et al. . |
| 4,066,073 | 1/1978 | Finney et al. . |
| 4,151,840 | 5/1970 | Barrington . |
| 4,151,841 | 5/1979 | Barrington . |
| 4,176,411 | 12/1979 | Runge . |
| 4,187,839 | 2/1980 | Nuwayser et al. . |
| 4,201,202 | 5/1980 | Finney et al. . |
| 4,204,530 | 5/1980 | Finney . |
| 4,224,934 | 9/1980 | Scott et al. . |
| 4,235,227 | 11/1980 | Yamanaka . |
| 4,267,829 | 5/1981 | Barton et al. . |
| 4,318,396 | 5/1982 | Finney . |
| 4,335,714 | 6/1982 | Edgerton et al. . |
| 4,353,360 | 10/1982 | Finney et al. . |
| 4,369,771 | 1/1983 | Trick . |
| 4,392,562 | 7/1983 | Burton et al. . |

FOREIGN PATENT DOCUMENTS

| | | |
|---|---|---|
| 714925 | 5/1946 | Fed. Rep. of Germany . |
| 7805284 | 2/1978 | Fed. Rep. of Germany . |
| 2740263 | 3/1979 | Fed. Rep. of Germany . |

*Primary Examiner*—Stephen C. Pellegrino
*Attorney, Agent, or Firm*—Merchant, Gould, Smith, Edell, Welter & Schmidt

[57] ABSTRACT

A penile prosthesis (20) designed to be surgically implanted in the penis for the treatment of erectile impotence. The prosthesis comprises an articulated column (26) having alternating joints (56) enclosed with a switch (30) within an outer elongated sheath (28). The switch (30) is aligned for reversibly extending the articulated column (26) against the ends of the sheath and tensioning a tension member (32) whereby frictional resistance at the joints (56) increases causing an erect state.

6 Claims, 11 Drawing Figures

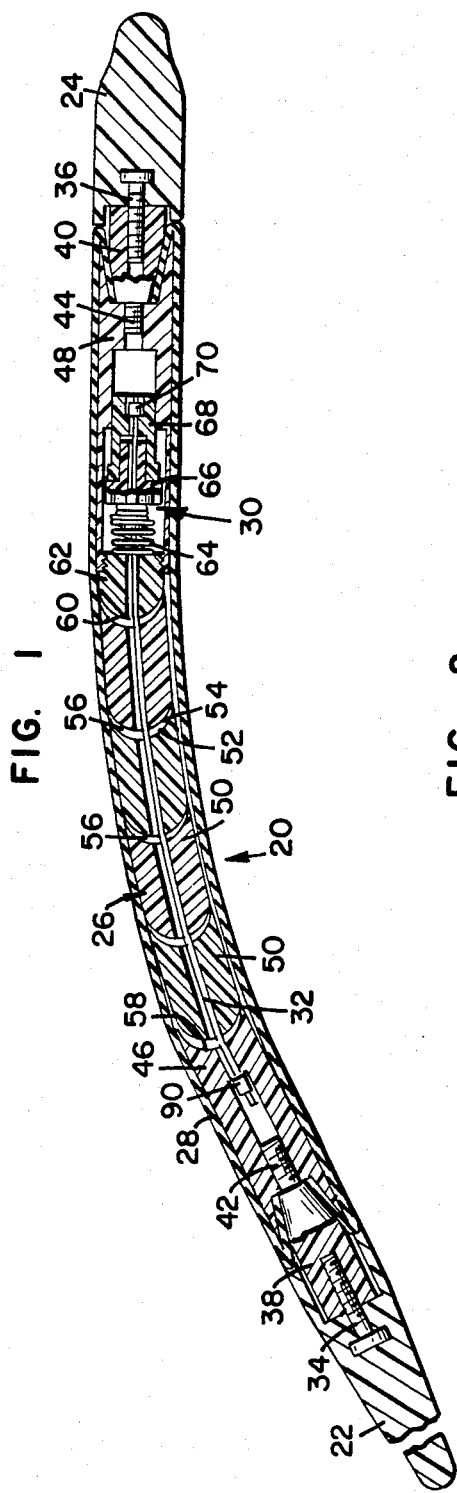
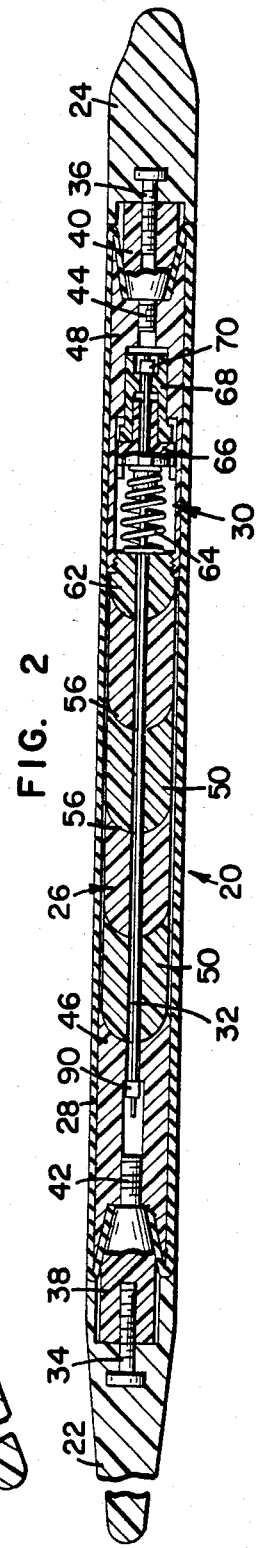
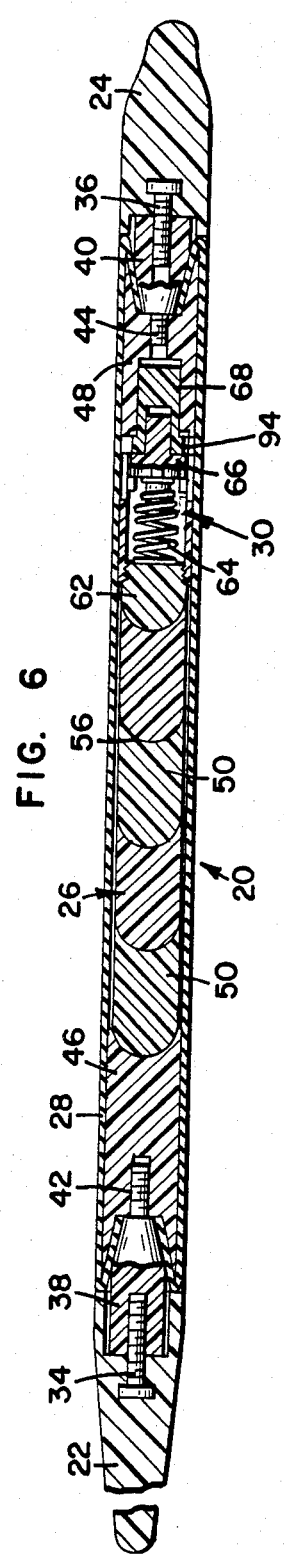

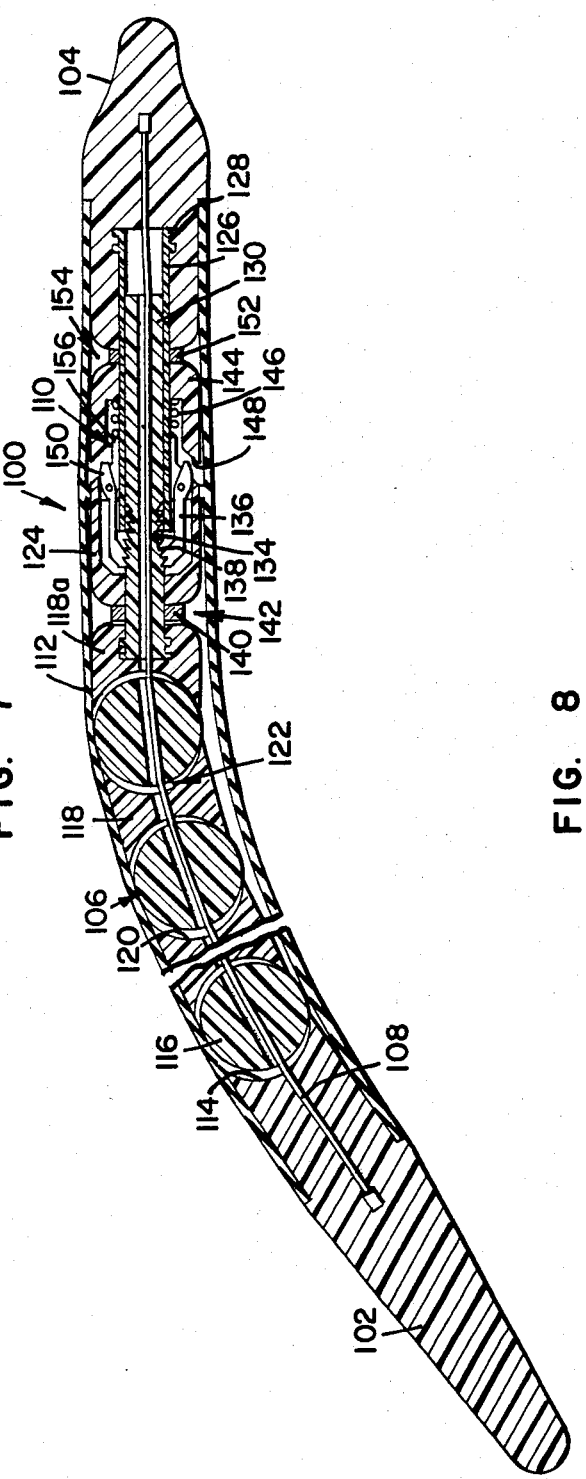
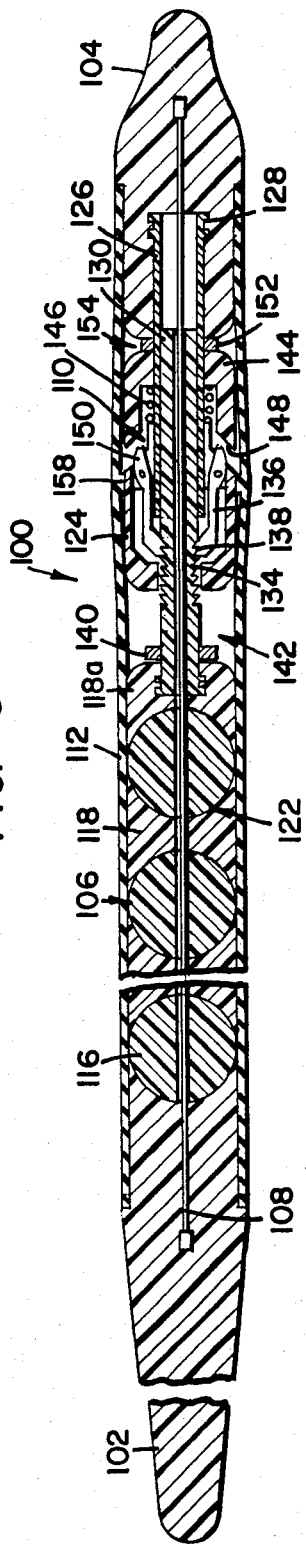

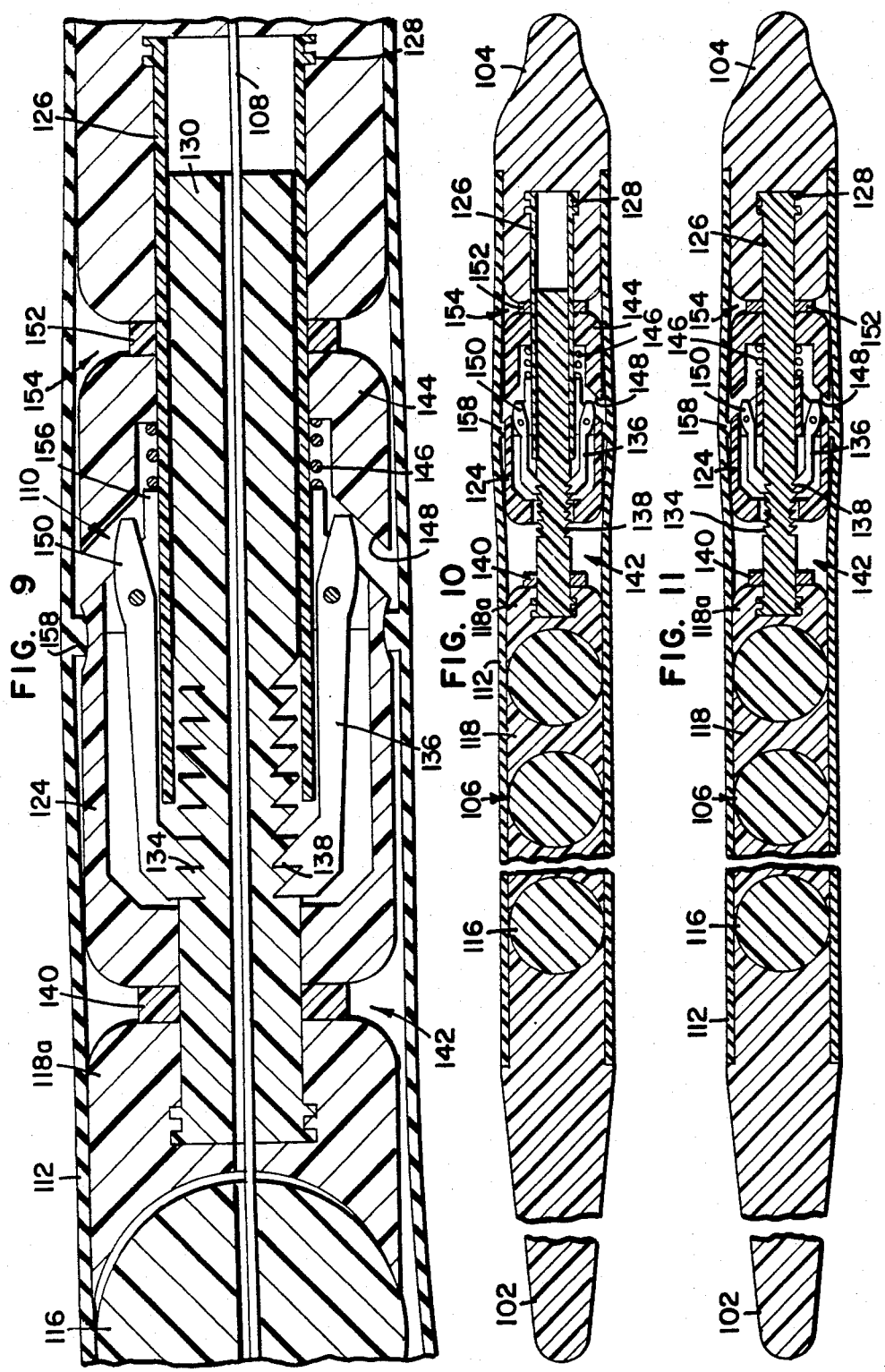

PENILE PROSTHESIS

BACKGROUND OF THE INVENTION

This invention relates to the treatment of erectile impotence. More particularly, the present invention relates to a penile prosthesis which may be implanted in a flaccid penis for enabling the achievement of an erectile state.

The causes of male impotence are many and varied. Various approaches to treating impotence have been developed over the past two decades. Penile prostheses implanted within the penis to simulate an erectile state are shown for example in Timm et al U.S. Pat. No. 3,987,789. That patent shows a prosthesis including an elongated malleable rod portion housed within a generally tubular physiologically inert plastic body. The malleable rod portion enables the prosthesis to be conformed to a variety of shapes by bending or twisting. During intercourse the prosthesis will maintain the penis in an erectile state and afterwards the penis may be positioned and maintained by the user in a convenient, comfortable position. The prosthesis depends upon its malleability to permit moving the penis to a convenient comfortable position. The flexibility and similar characteristics of the prosthesis are not controllable by the patient.

U.S. Pat. No. 3,954,102 to Buuck shows a penile erection system having two conditions. In one condition, the implanted prosthesis is controlled by varying the amount of fluid in cylinders within the prosthesis by squeezing an elastomeric bulb through the patient's skin to transfer fluid from a reservoir into cylinders in the prosthesis. Because the reservoir and bulb are positioned outside of the prosthesis within the patient's body, the implantation procedure is quite complex and the extensive tubing required to interconnect the various portions of the system increase the possibility of failure of the system.

Other implantable prostheses have been developed which incorporate a reservoir pump and valving into the prothesis itself as shown for example, in Patent Nos. 4,369,771 and 4,353,360. Those systems still require pump and valving apparatus to be installed within the prosthesis and require the transfer of fluid from a reservoir into an inflatable portion for operation.

The present invention solves these and many other problems associated with currently available devices.

SUMMARY OF THE INVENTION

The present invention relates to a penile prosthesis for implantation in a penis. The prosthesis includes an outer elongated sheath formed from a physiologically inert and pliable material. The sheath encloses an articulated column of segments having slidable joints therebetween and further encloses a switch means. A tension means extends longitudinally of the prosthesis. The switch means is operatively interconnected to the tension means and the articulated column for increasing the tension of the tension means and compressing the articulated column when activated by a user, thereby the frictional resistance of the joints of the articulated column is increased, thereby imparting rigidity to the prosthesis.

The invention provides for a mechanical patient-controlled device for inducing penile erection upon manual activation. In particular, the invention is a surgically implantable mechanical penile prosthesis composed of an elongated cylindrical device which employs an articulated column characterized by a series of segments with slidable alternating ball and socket joints therebetween. The normal flexibility of the device permits the penis to normally remain in a flaccid state.

The prosthesis of the present invention is particularly advantageous in that it can be implanted surgically without regard to angular orientation thereby avoiding the possibility of failure if during implant or in use, the prosthesis partially rotates about its longitudinal axis. Accordingly, the prosthesis is designed to be generally symmetrical about its longitudinal axis.

Furthermore, the present invention provides for volitional control of erection, generating sufficient stiffness of the penis for intercourse, and permits user deactivation, whereby the penis recovers as a flaccid state.

Yet another advantageous feature of the present invention is that it readily enables patient activation and deactivation.

Furthermore, the present invention is designed to be implanted by standard surgical procedures and is biologically compatible with the human body environment.

In addition, the present invention provides for activation/deactivation over many cycles of use.

Furthermore, the present invention enables the penis to obtain a flaccid-like state when the prosthesis is deactivated and provides sufficient rigidity for intercourse when the prosthesis is activated.

A preferred embodiment of the present invention is bistable. In other words it operates in either a flexible or a stiffened mode at the user's control. Activation and deactivation is achieved by manual bending of the penis, whereupon the prosthesis is alternately rigid or flaccid. Bending of the prosthesis places a tension member in tension which causes a switch apparatus to be axially displaced in a proximal direction, the switch apparatus including a locking mechanism for alternately securing the prosthesis in a deactivated position.

In one embodiment of the present invention, the articulated column is axially journaled about the longitudinally extending tension member. When the prosthesis is activated, the increased tension in the tension member and the compression of the articulated column induces a stress state in the prosthesis that displays bending stiffness. This is attributable to: (1) Interfacial friction between the spheres and sockets in the column; (2) tension in the tension member; and (3) friction between the sheath and the internal articulated column along the cylindrical circumference of the prosthesis.

In one embodiment of the present invention, the penile prosthesis, when implanted longitudinally in the corpora cavernosa of the penis is switched from one condition to another by repetitive compressive palpations of the penis at activation or deactivation sites readily locatable by finger palpation of the implanted prosthesis. The prosthesis characteristics are controlled by a switch placed between the ball and socket joints and the distal tip of the prosthesis. Compressive palpation of the activation site causes the switch to longitudinally extend itself against the column of segments until the increased frictional resistance between the joints results in a relatively rigid penis.

In one embodiment, the mechanical penile prosthesis achieves erection by tensioning an internal, axially extending elongated tension member by axial elongation of the penis.

The mechanical switch or actuating mechanism transduces radial pressure from the fingers to axial motion, thereby elongating the region of the switch assembly. The switch is enclosed within the external sheath such that its induced axial elongation forces the internal column against the inner wall of the sheath, causing it to expand and exert force in the articulated column, restricting its "bendability" and stiffening the device.

The switch in one embodiment generates axial displacement under the influence of radial force directed normal to the axis of the device at the activation site. It is preferable that the switch be designed to be symmetrical about its major axis in the context of its operating elements. The switch is activated and deactivated at separate and unique sites along the longitudinal axis of the device thereby permitting the user to select between stiff or flaccid modes of the prosthesis.

In one embodiment, the switch includes a capsule or retaining case which is connected to the external sheath and a release collar. The capsule includes a ratchet which can be urged along an underlying toothed support rod which is connected to the distal tip and a ball and socket of the articulated column. When radial finger pressure is applied to the penis and prosthesis at the activation site, the switch capsule moves distally up the support rod, away from the articulated column of balls and sockets. The sheath from the proximal end to its attachment point on the switch becomes taut, inducing an erection. Deactivation of the prosthesis is achieved by finger palpation at the release collar site causing the ratchet to release from the support rod to permit the capsule to slide proximally releasing the tension on the sheath, and returning the prosthesis to its flexible state.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views:

FIG. 1 is a longitudinal axial sectional view of a preferred embodiment of the present invention in a deactivated or flaccid state;

FIG. 2 is a longitudinal sectional view of the embodiment shown in FIG. 1 in an activated or rigid state;

FIG. 6 is a longitudinal view of an alternate embodiment of the present invention wherein an outer sheath is operatively interconnected to the switch apparatus;

FIG. 7 is a fragmentary longitudinal axial sectional view of yet another embodiment of the present invention in a flaccid state;

FIG. 8 is a fragmentary longitudinal axial sectional view of the embodiment shown in FIG. 7 in an activated state;

FIG. 9 is an enlarged fragmentary sectional view of a switch apparatus of the embodiment shown in FIG. 7 in a deactivated state;

FIG. 10 is a fragmentary longitudinal axial sectional view of still another embodiment of the present invention; and FIG. 11 is yet another embodiment of the present invention.

DETAILED DESCRIPTION OF A PREFERRED EMBODIMENT OF THE INVENTION

Figure 3:
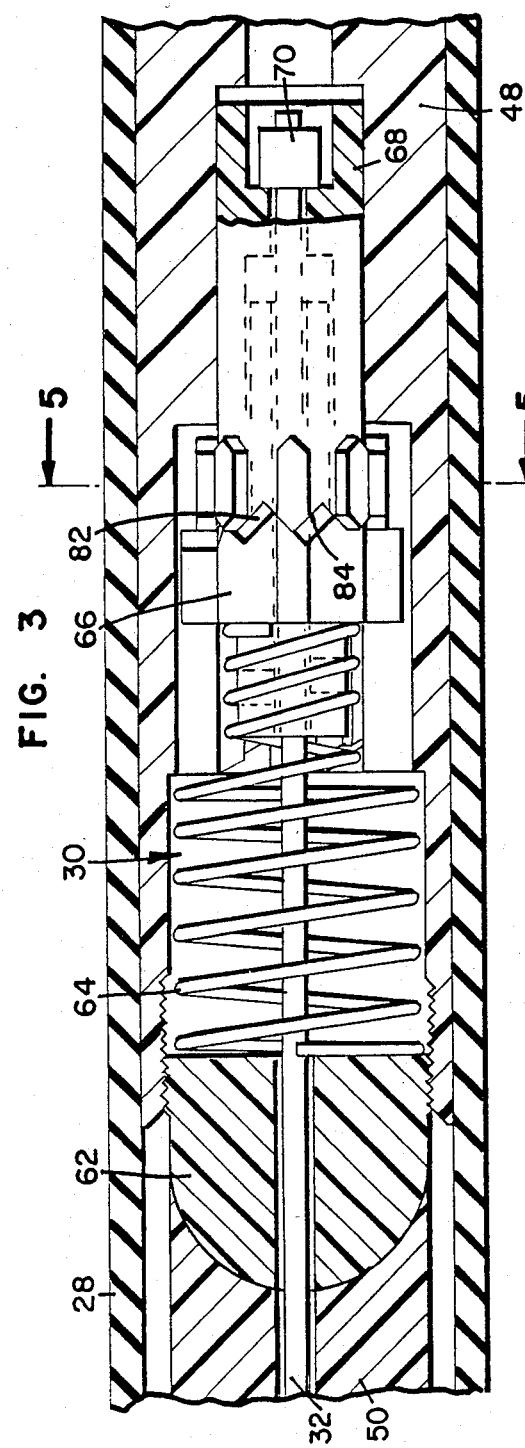
FIG. 3 is an enlarged axial sectional view with portions broken away of the switch apparatus of the embodiment shown in FIG. 2 in an activated state.

Referring now to the drawings, a preferred embodiment of a mechanical penile prosthesis in accordance with the principles of the present invention is illustrated in FIGS. 1 and 2, the penile prosthesis generally being referred to by the reference numeral 20. The prosthesis 20 is generally shown as an elongated member including a proximal end portion 22 and a distal end portion 24. An elongated articulated column 26 is positioned between the proximal and distal end portions 22 and 24 enabling pivotal or bending motion of the prosthesis 20 in all directions (360 degrees) about the longitudinal axis of the prosthesis 20. Interposed between the distal end of the articulated column 26 and the distal end portion 24 is a switch apparatus 30. The articulated column 26 and the switch apparatus 30 are axially journaled about an axially extending elongated tension member 32 which extends from proximate the proximal end of the articulated column 28 to proximate the distal end of the switch apparatus 30. The articulated column 26 and the switch apparatus 30 are enclosed by a sheath 28 of physiologically inert and pliable material which shields the prosthesis 20 from body fluids so as to prevent their interference with the functioning of the prosthesis 20.

It will be appreciated that while for purposes of this specification the prosthesis is described as having proximal and distal ends, and in the embodiments shown, the switch apparatus is located proximate the distal end, the switch apparatus in keeping with the principles of the present invention might be located anywhere intermediate of the first or second ends without regard to the proximal or distal location of the first and second ends.

The switch apparatus 30 in cooperation with the tension member 32 and the articulated column 26 provides the preferred embodiment of the present invention with bistable characteristics, i.e. the prosthesis 20 may be manually activated to a rigid/activated state as generally illustrated in FIG. 2 or deactivated to a flexible/flaccid state as generally indicated in FIG. 1. The prosthesis 20 remains in either of these two states until manually activated or deactivated.

The prosthesis 20 of the present invention is designed for implantation in the corpora of the penis by standard surgical procedures for treatment of erectile impotence. The prosthesis 20 is configured to generally match penile corpora size so as to extend sufficiently proximally and distally when anchored within the penis and body cavity so as to induce an erected penile state generating sufficient stiffness of the penis for intercourse when activated and to provide the penis with flaccid characteristics when deactivated.

Accordingly, the present invention provides for volitional control of penile erection and return thereof to a flaccid state. Furthermore, the configuration of the present invention enables surgical implantation without regard for angular orientation and prevents malfunction if angular rotation is realized during use. In addition, the present invention is biologically compatible with the human body environment and enables activation/deactivation over many repetitive cycles of use.

More particularly, the proximal end portion 22 is tapered to assist in anchoring the prosthesis 20 in the body and the distal end portion 24 is bullet- or cone-shaped to adapt to the distal end of the penis. The proximal end portion 22 and the distal end portion 24 are provided in various lengths, preferably ranging from one to four centimeters. The appropriate length for each is selected at the time of implant as determined by the incision site and by the patient's total intracorporeal length. Preferably, the proximal end portion 22 and the distal end portion 24 are made from a semi-rigid material such as silicon rubber.

The proximal end portion 22 and the distal end portion 24 are attached to the segmented, flexible body of the prosthesis 20. This might be accomplished in any of several ways such as by a positive locking, snap-on mechanism (not shown) or by threaded attachment of the end portions 22, 24 to the flexible body of the prosthesis 20. This is accomplished in the preferred embodiment as generally illustrated in FIGS. 1 and 2 by elongated threaded members 34, 36 securely embedded in the proximal end portion 22 and the distal end portion 24, respectively, which are threaded into clamp members 38, 40, respectively. The clamp members 38, 40 in turn are threadedly attached to the flexible body of the prosthesis by elongated threaded members 42, 44, respectively. The clamp members 38, 40 cooperate with members 46, 48, which are configured to receive the clamp members 38, 40 such that the end portions of the sheath 28 are wedged between the clamp members 38, 40, and the inside sloping walls of the members 46, 48. Accordingly, the sheath 28 is retained in position at the proximal and the distal end portions of the prosthesis 20.

The articulated column 26 comprises a plurality of cylinders 50. Each of the cylinders 50 has a concave surface 52 and a convex surface 54, the cylinders 50 being oriented such that the adjacent surfaces of the cylinders cooperate to form ball and socket joints 56. The articulated column 26 is journaled axially to receive the tension member 32. The cylinders 50 as well as the other internal parts of the prosthesis are made from a surgically implantable material, preferably an implantable plastic, such as polyurethane.

It will be appreciated that in alternate embodiments of the present invention, other elements with slidable cooperating surfaces may be utilized to form an articulated column. For example, as illustrated in FIGS. 7 and 8, the articulated column might be formed of alternating cylinders and spheres forming interfitting ball and socket joints. Yet another example is that of U.S. Pat. No. 4,151,840 (Barrington) wherein the cylinders of the articulated column have modified convex and concave surfaces.

In the embodiment illustrated, the cylindrical member 46 to which the sheath 28 is clamped, has a generally concave surface 58 adjacent the proximal end of the articulated column 26 to form a ball and socket joint with the articulated column 26.

Furthermore, a proximal end portion 62 of the cylindrical member 48 has a convex surface 60 thereby forming a ball and socket joint with the articulated column 26.

Interposed between the distal end of the articulated column 26, and the distal end portion 24 is the switch apparatus 30. As previously discussed, in the preferred embodiment shown, the cylindrical member 48 which cooperates with the clamp member 40 in retaining the sheath 28 at the proximal end of the prosthesis 20, also functions as the housing for the switch apparatus 30. The proximal end portion 62 of the housing 48 is illustrated as being threadedly attached to the housing 48 to facilitate assembly of the switch apparatus 30.

Figure 4:
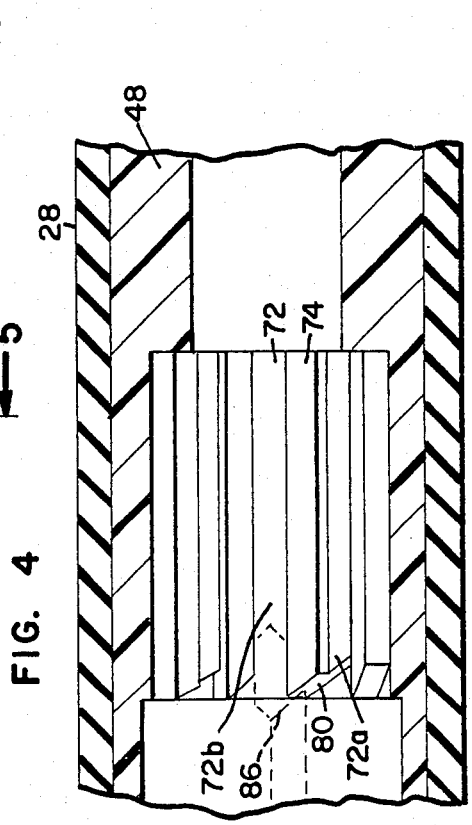
FIG. 4 is a further enlarged sectional view of a portion of the switch apparatus shown in FIG. 3 with parts thereof removed for clarity of illustration.

As illustrated in FIG. 3, positioned within a cavity of the housing 48 are a coil spring 64, a rotary actuator 66, and a sliding actuator 68 which is securely attached to the distal end of the tension member 32 at location 70. As further illustrated in FIGS. 3-5, the inside surface of the housing 48 includes a plurality of axially extending alternating grooves 72 and ridges 74 along a portion thereof, which serve as guides for spaced-apart ridges 76, 78 positioned about the circumference of the actuators 66, 68, respectively so as to maintain the relative positioning of the rotary actuator 66 with respect to the sliding actuator 68. Furthermore, the proximal ends of the grooves 72 and ridges 74 are oblique with respect to the longitudinal axis such that an adjacent groove and ridge cooperate to form a continuous sloping surface 80. The adjoining end portions 82, 84 of the rotary actuator 66 and the sliding actuator 68 have a saw-toothed configuration to form a gear-like meshing therebetween. The spaced apart ridges 76, 78 about the circumference of the rotary actuator 66 and the sliding actuator 68 are positioned such that when the actuators 66, 68 are positioned in the grooves 72 of the housing 48, the end portions 82, 84 of the actuators are offset or staggered as generally illustrated in FIG. 3. Accordingly, when the rotary actuator 66, is positioned outside of the housing grooves 72, the rotary actuator 66 will rotate about the longitudinal axis so as to align itself with the saw-toothed configuration of the sliding actuator end portion 84 as illustrated by the broken lines 86 in FIG. 4. When the rotary actuator 66 moves toward the distal end of the prosthesis 20, the oblique surfaces 80 of each of the cooperating housing ridges 74 and grooves 72 will cause the rotary actuator 66 to again rotate about the longitudinal axis of the prosthesis 20 such that the rotary actuator 66 is once again offset from the saw-toothed configuration of the sliding actuator end portion 84.

Figure 5:
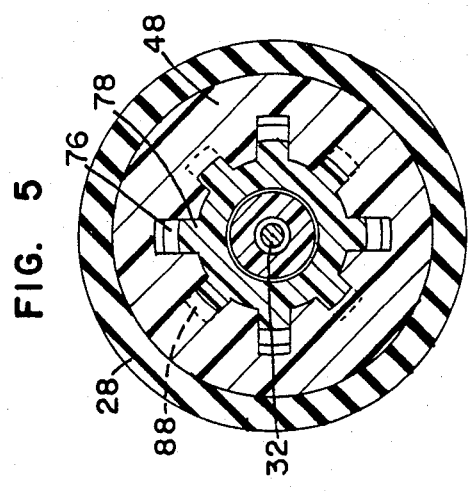
FIG. 5 is a transverse sectional view as generally seen along line 5—5 of FIG. 3.

In addition, as illustrated in FIG. 5, while there are eight of the housing grooves 72, alternating ones of the grooves 72a do not extend radially as far as the others of the grooves 72b. Furthermore, as illustrated in FIG. 5, the ridges 76 of the rotary actuator 66, there being four in number, extend further radially than the grooves 72a, while the ridges 78, there being eight in number, of the sliding actuator 68 do not extend radially as far as the grooves 72a. The rotary actuator 66 and the sliding actuator 68 are configured such that when the rotary actuator 66 extends beyond the grooves 72 it will rotate one-eighth of a revolution such that the rotary actuator ridges 76 will alternately engage the housing grooves 72a as generally illustrated by the broken lines 88 in FIG. 5 and alternately slide toward the distal end of the prosthesis in the grooves 72b. Accordingly, the rotary actuator 66 is alternately locked in a deactivated position wherein the prosthesis 20 is generally flaccid and unlocked so as to move distally of the prosthesis into an activated position wherein the prosthesis 20 is relatively rigid.

The coil spring 64 positioned between the proximal end portion 62 of the housing and the rotary actuator 66 biases the actuators 66, 68 toward the distal end of the prosthesis 20. As previously indicated, the tension member 32 is attached to the sliding actuator 68 at the location 70 and is further attached to the member 46 at location 90. Accordingly, the biasing effect of the coil spring 64 is overcome by placing the axial tension member 32 in sufficient tension such that the force exerted by the rotary actuator 66 and the sliding actuator 68 on the coil spring 64 is greater than that of the coil spring 64, whereby the rotary actuator 66 and the sliding actuator 68 are caused to move toward the proximal end of the prosthesis 20, thereby causing the rotary actuator 66 to rotate upon moving beyond the housing grooves 72. The tension member 32, which is preferably pre-stretched prior to assembly, is placed in tension by bending the prosthesis 20 due to its fixed length. The applicant has found that a tension member made from braided stainless steel provides the preferred characteristics of lightweight, strength, and resistance to the corrosive effects of body fluids.

It will be appreciated that the above described switch apparatus is not unlike that of a ballpoint pen actuator mechanism and that varying embodiments of the switch apparatus 30 in keeping with the principles of the present invention might be utilized.

As previously indicated, the entire prosthesis 20 is preferably covered with the sheath 28 of physiologically inert and pliable material to shield the prosthesis from body fluids and prevent interference with its functioning, the sheath 28 being wedgedly secured by the clamp members 38, 40 in cooperation with the members 46, 48 near the proximal and distal ends of the prosthesis 20. The applicant has found that expanded polytetrofloralethylene (PTFE) such as the product sold by Dupont Corporation under the trademark Teflon is a suitable material.

In use, the implanted prosthesis 20 is normally maintained in an untensioned or flaccid state which does not interfere with bending or moving of the penis. Accordingly, the rotary actuator 66 is locked in its deactivated position such that the tension member 32 is not in tension. This lack of tension allows the surfaces 52, 54 of the cylindrical members 50 forming the ball and socket joints 56 of the acticulated column 26, to freely slide relative to each other under low friction conditions thereby providing the prosthesis 20 and thus the penis with flexibility as though in a flaccid, non-erect state.

To provide an erection, the user manually bends the prosthesis 20 which results in increased tension in the fixed length tension member 32. When the force exerted by the tension member 32 exceeds that of the coil spring 64, the rotary actuator 66 and the sliding actuator 68 are displaced axially toward the proximal end of the prosthesis 20. As previously described, configuration of the rotary actuator 66 and the sliding actuator 68 is such that the rotary actuator 66 is caused to rotate about its axis when axially displaced a predetermined amount, whereby the rotary actuator 66 is unlocked from its deactivated state. Accordingly, when the prosthesis is straightened, the rotary actuator 66 and the sliding actuator 68 are axially displaced toward the distal end of the prosthesis 20 by the coil spring 64 to a location closer to the distal end of the prosthesis 20 then when in the deactivated state. Accordingly, a degree of tension is induced in the tension member 32 and the articulated column 26 is compressed due to the biasing effect of the coil spring 64. As a result of the increased tension and compression of the articulated column 26, the frictional force between the radiused ends of the cylindrical members 50 is increased such that the prosthesis 20 and correspondingly the penis are in a rigid or erect state. Furthermore, friction between the sheath 28 and the articulated column 26 along the longitudinal circumference contributes to the overall rigidity or stiffness of the prosthesis 20.

Subsequent restoration of the penile flaccidity or flexibility is achieved by again bending the prosthesis 20 into a curved shape. Tension in the tension member 32 is increased to a point where it exerts a force which exceeds that of the biasing effect of the coil spring 64, whereby the rotary actuator 66 and the sliding actuator 68 are axially displaced in a proximal direction. The rotary actuator 66 is caused to rotate about its axis upon moving axially beyond the grooves 72 in the housing 48 such that the rotary actuator 66 is again locked in a deactivated position at a location closer to the proximal end of the prosthesis 20 than when in the activated state. Accordingly, tension in the tension member 32 is again reduced enabling the ball and socket joints 66 of the articulated column 26 to exhibit a high degree of freedom of movement such that the prosthesis 20 and correspondingly the penis is again in the flaccid state.

Subsequent bending and unbending may be carried out for numerous repetitions with the prosthesis 20 being alternately rigid and flaccid. The prosthesis 20 thus exhibits bistable characteristics in that it maintains either of the states until being manually changed.

An alternate embodiment of the present invention which does not utilize the axial tension member 32 is illustrated in FIG. 6. In this embodiment, the sliding actuator 68 of the switch apparatus 30 is attached to the sheath 28. Accordingly, the sheath 28 is alternately placed in tension and loosened upon bending of the prosthesis 20. In this manner, the prosthesis 20 is alternately placed in a rigid or flaccid state by a procedure not unlike that of the previous embodiment. In the embodiment illustrated, sliding actuator 68 is attached at 94 to the sheath 28 although it will be appreciated that various methods of attachment to the sliding actuator 30 in keeping with the principles of the present invention might be utilized.

In this embodiment, some, such as alternating ones, or all of the segments of the articulated column might be made of a softer material. Accordingly, upon compression of the articulated column the softer segments will bulge outwardly against the sheath 28 so as to provide additional friction and rigidity.

FIGS. 7–9 illustrate yet another embodiment of the present invention generally designated by the reference numeral 100. The prosthesis 100 includes a proximal end portion 102 and a distal end portion 104. An articulated column 106, somewhat like that of the previous embodiments, is journaled axially about a tension member 108 and is positioned between the proximal end portion 102 and the distal end portion 104. A switch apparatus 110, somewhat unlike that of the previous embodiments, is interposed between the distal end portion 104 and the articulated column 106. The prosthesis 100, as with the previous embodiments, is enclosed by a sheath 112 of physiologically inert and pliable material to shield the prosthesis from body fluids and prevent interference with its functioning. Sheath 112 also may be utilized to assist in providing rigidity to the prosthesis 100 when in an activated or rigid state. As with the previous embodiments, the prosthesis 100 is manually switchable from an activated or rigid state to a deactivated or flaccid state.

More particularly, the tension member 108 extends from the proximal end portion 102 wherein it is securedly embedded to the distal end portion 104 wherein it is also securedly embedded. The proximal end portion 102 is configured to function as an anchoring support for the prosthesis 100 in the user's body and is further configured with a concave surface 114 at its distal end to provide a ball and socket joint with the articulated column 106. As with the previous embodiments, the embodiment illustrated in FIGS. 7-9 may be implanted using conventional surgical techniques.

Preferably, the proximal end portion 102 is formed from a material such as silicon rubber which may be readily trimmed to provide a length and diameter configured to match the patient's corpora size. The distal end portion 104, preferably bullet- or cone-shaped, is adapted for the distal end of the penis.

The articulated column 106 which is positioned longitudinally between the proximal end portion 102 and the distal end portion 104 includes a plurality of alternating spheres 116 and cylindrical members 118. The cylindrical members 118 define concave surfaces 120 at their ends such that the adjoining concave surfaces 120 of the cylindrical members 118 and the spheres 116 form ball and socket joints 122. The concave surface 114 of the distal end portion 102 cooperates with one of the spheres 116 at the proximal end of the articulated column 106 to form a ball and socket joint therebetween. The spheres 116 and the cylindrical members 118 are journaled axially about the tension member 108. As previously discussed, it will be appreciated that in alternate embodiments of the present invention other elements might be utilized with slidable cooperating surfaces to form the articulated column 106 in keeping with the principles of the present invention.

In various embodiments, the spheres 116 might have indentations in the surfaces thereof and the cylindrical members 118 corresponding protrusions in the surfaces thereof. Accordingly, when the articulated column is compressed, the indentations and protrusions cooperate with each other to increase the overall friction of the ball and socket joints.

The switch apparatus 110 is positioned between the distal end portion 104 and the distal end of the articulated column 106. It will be appreciated that the switch apparatus 110 could also be located at other locations along the prosthesis 110. The switch apparatus 110 provides for control of axial elongation of the prosthesis 100 resulting in compression of the articulated column 106 and tensioning of the tension member 108. As illustrated in FIG. 9, the switch apparatus 110 includes a retaining case 124 fixedly secured to a sleeve member 126 which extends axially into the distal end portion 104 where it is anchored by flange portions 128. The sleeve member 126 slidably receives a shaft member 130 which is secured at its proximal end to a modified cylindrical member 118a of the articulated column 106 by flange portions 132. As illustrated, the shaft 130 and the cylindrical member 118a are axially journaled to allow the tension member 108 to pass axially therethrough. The shaft 130 is formed with serrated engagement points 134 on its outer surface along at least a portion thereof. Retaining case 124 extends axially beyond the proximal end of the sleeve member 126 and is journaled to allow the shaft 130 to slide therethrough.

The retaining case 124 includes a pair of pivoting arms or pawls 136 with serrated teeth 138 which are configured to ratchet distally along serrations 134 of the shaft 130. A spacer member 140 fixedly secured on the shaft 130 between the articulated column 106 and the retaining case 124 has a lesser diameter than either the articulated column 106 or the retaining case 124 whereby an indentation or activation site 142 is formed which may be felt by touch. Transcutaneous radial pressure from a user's finger(s) at the activation site 142 is transduced to generally axial elongation of the switch apparatus 110 by causing a ratcheting action of the pawls 136 along the shaft 130 whereby the prosthesis 100 is positioned in an erect or rigid state.

A release member or collar portion 144 is axially, slidably positioned about the sleeve 126 between the retaining case 124 and the distal end portion 104. The release member 144 is separated from release ends 150 of the pawls 136 by a coil spring 146 positioned about the sleeve 126 and abutting a distal lip portion 156 of the retaining case 124. The release member 144 includes a beveled portion 148 which when forced axially in a proximal direction engages the release ends 150 of the pawls 136 thereby causing disengagement of the pawls 136 from the serrations 134 of the shaft 130. The spring 146 biases the collar portion 144 away from the release ends 150 of the pawls 136 to prevent the beveled portion 148 of the collar 144 from engaging the pawls 136 so as to accidentally cause disengagement of the pawls 136 from the shaft 130. However, upon manual application of sufficient force, the spring tension is overcome and the pawls 136 released. A spacer 150, fixedly secured to the sleeve 126 between the collar portion 144 and the distal end portion 104 and further being of less diameter than the collar portion 144 and the distal end portion 104, provides a readily discernable release site 154 which may be palpated to overcome the bias of the spring 146 thereby releasing the prosthesis 100 from its erect, rigid state and placing the prosthesis 100 in a flaccid state.

As with previous engagements, the external cylindrical sheath 112 is preferably formed from a physiologically inert material such as silicon rubber, Dacron, expanded PTFE, etc. and encases the prosthesis 100 in a fluid-tight manner. In the embodiment illustrated in FIGS. 7-9, the sheath is attached to the retaining case 124 at a sheath attachment portion 158.

In use, the implanted prosthesis is normally maintained in an untensioned state which does not interfere with bending or moving the penis. The pawl teeth 138 engage the shaft teeth 134 at the proximal end of the shaft 130, as generally illustrated in FIG. 7. In this condition, the prosthesis 100 is at its minimum length and the tension member 108 is untensioned. This lack of tension allows the surfaces of the ball and socket joints 122 of the articulated column 106 to slide relative to each other under a low friction condition so as to move freely, maintaining flexibility to the prosthesis in the penis as shown in FIG. 7.

To provide an erection, the user manually applies repetitive palpations at the activation site 142. The radial force is transduced to axially elongation of the prosthesis by causing a ratcheting effect and relative translational movement between the pawls 136 and the shaft 130.

When the device is actuated, the shaft 130 is displaced proximally, sliding away from a distal end of the sleeve 126 as illustrated in FIG. 8. This increases the length of the prosthesis 100 and the tension member 108 is accordingly placed under tension. Furthermore, the articulated column 106 is compressed due to displacement of the shaft 130. Accordingly, the increased tension in the tension member 108 and compression of the articulated column 106 decreases the separation between each of the ball and socket joints 122, thereby increasing frictional resistance to movement. Friction between the sheath 112 and the internal articulated column 106 along the longitudinal circumference also may contribute to the overall rigidity of the prosthesis 100.

It has been found that an axial elongation of two to six milimeters will generate adequate tension to maintain an erection.

Restoration of penile flexibility is achieved by finger palpations at the deactivation site 154. The application of radial pressure causes the release member 144 to move proximally against the spring 146 until the beveled portion 148 contacts the pawl release ends 150 which disengage the pawls 136 from the shaft 130. Flaccidity is restored as the shaft 130 slides distally along the sleeve 126 such that tension in the tension member 108 is reduced.

It will be appreciated that the prosthesis may be deactivated and activated repetitively numerous times. Furthermore, once positioned in either a flaccid state or a rigid state, the prosthesis 100 will remain in the state where currently positioned until manually changed thereby providing for user volitional control. In addition, the embodiments shown in FIGS. 7–9 provide for varying degrees of rigidity as the pawls 136 ratchet distally along the shaft 130.

Yet another embodiment of the present invention is shown in FIG. 10 which does not utilize an axial tension member. In this embodiment, the sheath 112 is utilized as the primary tensioning member.

Still yet another embodiment of the present invention is shown in FIG. 11. Once again, the sheath 112 is utilized as the tensioning member as opposed to an axial tension member; however, the embodiment shown in FIG. 11 is generally of fixed length as the distal end portion 104 is attached directly to the shaft 130. Accordingly, as the switch apparatus 110 moves distally on the shaft 130, the sheath 112 is placed in tension but the overall length of the prosthesis changes very little if at all. In this embodiment, the sheath 112 is preferably relatively unstretchable, as the sheath 112 may include woven layers to provide adequate strength to resist stretching as the prosthesis is operated.

It is to be understood, however, even though numerous advantages and characteristics of the invention have been set forth in the foregoing description, together with details of the structure and function of the invention, the disclosure is illustrative only, and changes may be made in detail, especially in matters of shape, size and arrangement of parts within the principles of the present invention, to the full extent indicated by the broad general meaning of the terms in which the appended claims are expressed.

What is claimed is:

1. A penile prosthesis, comprising:
a. a first end;
b. a second end;
c. an outer elongated sheath formed from physiologically inert and pliable material;
d. an articulated column of segments having slidable joints therebetween and enclosed within said sheath;
e. switch means for switching the prosthesis between a rigid condition and a flaccid condition, said switch means disposed intermediate of said articulated column and the first end of the prosthesis and enclosed within said sheath, said switch means including an axially slidable portion interconnected to a first end of elongated tension means which is fixedly secured at a second end proximate the second end of the prosthesis; said tension means cooperating with said articulated column for imparting rigidity to said prosthesis when said articulated column is compressed and said tension means is in a tensioned condition, and for imparting flexibility to said prosthesis when said tension means is in an untensioned condition and said articulated column is not compressed, said switch means having first and second operative states, said switch means compressing said articulated column and placing said tension means in a tensioned condition when in said first state and placing said tension means in an untensioned condition and said articulated column in a noncompressed state when in said second state; and
f. said switch means being alternately switched from one state to the other by axial displacement of the first end of said tension means under user control.

2. The penile prosthesis of claim 1, wherein said tension means includes a fixed length, longitudinally extending elongated tension member, said articulated column being axially journaled about said tension member, said tension member being secured at the second end of the prosthesis and interconnected to the axially slidable portion of said switch means near the first end of the prosthesis, said axially slidable portion being biased axially in a direction away from said articulated column toward the first end of the prosthesis by biasing means disposed intermediate of said axially slidable portion and said articulated column.

3. The penile prosthesis of claim 2, wherein said fixed length tension member is axially displaced by bending the prosthesis, said fixed length tension member being constructed and arranged to generate a tension force upon being axially displaced which is sufficient to overcome said biasing means on bending the prosthesis, whereby said axially slidable portion will be displaced axially in a toward said articulated column from a first position to a second position.

4. The penile prosthesis of claim 3, wherein said switch means includes a locking mechanism for alternately locking said axially slidable portion in said second position and releasing said axially slidable portion upon a predetermined axial displacement of said axially slidable portion toward said articulated column, said axially slidable portion being biased toward said first position by said biasing means upon being released by said locking mechanism whereby said tension member is placed in tension.

5. A penile prosthesis, comprising:
a. a first end portion;
b. a second end portion;
c. an outer elongated sheath formed from physiologically inert and pliable material;
d. an articulated column of segments having slidable joints therebetween and enclosed within said sheath;
e. an elongated fixed length, tension member including first and second ends extending generally along the longitudinal axis of the prosthesis, said elongated tension member being securedly attached near the second end to proximate the second end portion of the prosthesis, said articulated column being axially journaled about said tension member;

f. switch means disposed between said articulated column and the first end portion of the prosthesis for switching the prosthesis between a rigid condition and a flaccid condition, comprising:

(i) biasing means for providing a biasing force axially in a first direction away from said articulated column;

(ii) an axially slidable portion including a rotary member and a non-rotary member being biased in the first direction away from said articulated column by said biasing means, said biasing means being disposed intermediate of said rotary member and an end portion of said articulated column, said tension member being interconnected proximate the first end to said axially slidable portion, said axially slidable portion being slidable between a first position and a second position further removed from the first end of the prosthesis than said first position; and (iii) means for alternately locking said rotary member at said second position, said tension member being relatively untensioned when said rotary member is positioned at said second position whereby the prosthesis is relatively flexible, said tension member being placed under tension and said articulated column being compressed when said rotary member is positioned at said first position whereby the prosthesis is relatively rigid; and g. said tension member cooperating with said switch means to displace said axially slidable portion in a second direction toward said articulated column upon bending of the prosthesis which places the tension member in sufficient tension to overcome the force of the biasing means.

6. A penile prosthesis, comprising:

a. a first end portion;
b. a second end portion;
c. an outer elongated sheath formed from physiologically inert and pliable material;
d. an articulated column of segments having slidable joints therebetween and enclosed within said sheath;
e. switch means disposed between said articulated column and the first end portion of the prosthesis for switching the prosthesis between a rigid condition and a flaccid condition, said switch means including a portion axially slidable between a first position and a second position closer to said articulated column than said first position, said axially slidable portion being interconnected to said sheath, said axially slidable portion being displaced axially toward said second position upon application of sufficient tension in said sheath, said switch means including a locking mechanism for alternately locking said switch means in said second position and releasing said switch means, said switch means including biasing means for displacing said switch means toward said first position when released by said locking mechanism, said switch means placing said tension member in tension when in said first position.

* * * * *

UNITED STATES PATENT AND TRADEMARK OFFICE
CERTIFICATE OF CORRECTION

PATENT NO. : 4,522,198
DATED : June 11, 1985
INVENTOR(S) : Gerald W. Timm, et al.

It is certified that error appears in the above-identified patent and that said Letters Patent is hereby corrected as shown below:

Col. 1, line 42, delete "prothesis" and insert --prosthesis--.

Col. 7, line 46, delete "acticulated" and insert --articulated--.

Col. 11, line 13, delete "milimeters" and insert --millimeters--.

Col. 12, line 46, before "toward" insert --direction--.

Signed and Sealed this

Twenty-sixth Day of August, 1986

[SEAL]

Attest:

DONALD J. QUIGG

Attesting Officer

Commissioner of Patents and Trademarks